United States Patent
Gault (12)

(10) Patent No.: US 6,589,525 B2
(45) Date of Patent: Jul. 8, 2003

(54) METHOD AND DEVICE FOR PREPARING A DENTAL IMPLANT BY IMMERSION IN A CULTURE OF MESENCHYMAL CELLS

(75) Inventor: Philippe Gault, Orleans (FR)

(73) Assignee: Societe Anonyme Natural Implant, Brest (FR)

(*) Notice: Subject to any disclaimer, the term of this patent is extended or adjusted under 35 U.S.C. 154(b) by 110 days.

(21) Appl. No.: 09/833,002

(22) Filed: Apr. 12, 2001

(65) Prior Publication Data

US 2001/0055745 A1 Dec. 27, 2001

Related U.S. Application Data

(63) Continuation of application No. PCT/FR99/02462, filed on Oct. 12, 1999.

(30) Foreign Application Priority Data

Oct. 13, 1998 (FR) .............................. 98 12831

(51) Int. Cl.$^7$ ................................. C12N 5/00
(52) U.S. Cl. ............... 424/93.7; 435/289.1; 435/303.1
(58) Field of Search ............... 424/93.7, 289.1, 424/304.1, 305.1, 303.1

(56) References Cited

U.S. PATENT DOCUMENTS 4,872,840 A 10/1989 Bori ..................... 433/173

FOREIGN PATENT DOCUMENTS

| DE | 40 40 872 | 12/1993 |
| DE | 42 22 296 | 12/1993 |
| EP | 0 734 712 | 10/1996 |
| JP | 1-299563 | 12/1989 |
| WO | 97/45533 | 12/1997 |

OTHER PUBLICATIONS

Hanes et al. *Journal of Periodontology*, vol. 60, No. 4, Apr. 1, 1989, pp. 188–189.

*Primary Examiner*—Jean C. Witz
(74) *Attorney, Agent, or Firm*—Young & Thompson

(57) ABSTRACT

The present invention concerns a method of manufacturing a dental implant comprising:

preparing an implant composed of a root portion and a crown portion and constituted by an inert biocompatible material in a shape which is adapted to an extracted tooth;

immersing the root portion of said implant into a culture of undifferentiated mesenchymal cells in a culture medium the composition of which allows differentiation into cementoblasts and fibroblasts, over a period which is sufficient for said differentiation and for adhesion of cementoblasts to the root portion and the formation of a first layer of cementum and an alveolodental ligament primordium attached to said cementum;

recovering the implant carrying differentiated tissues affixed to its root portion.

19 Claims, 2 Drawing Sheets

METHOD AND DEVICE FOR PREPARING A DENTAL IMPLANT BY IMMERSION IN A CULTURE OF MESENCHYMAL CELLS

This is a continuation of co-pending international application No. PCT/FR99/02462 filed on Oct. 12, 1999, which designated the United States of America.

The present invention relates to integrated periodontal implants comprising cementum on the surface of the root and a ligament to connect the cementum to the bone alveolus, as in a natural tooth.

The invention pertains to a method for preparing the implant by bringing the implant into contact with undifferentiated mesenchymal stem cells under culture conditions to allow adhesion of cementoblasts and of alveolodental ligament to the root portion of the implant and implanting the implant carrying differentiated tissue cells.

The invention also relates to a cell culturing apparatus for preparing a dental implant. Finally, it relates to a method for replacing lost or compromised teeth with implants to which biological tissues and cells have been affixed using a suitable cell culture technique, to then obtain mouth cicatrisation by cementum and ligaments between the bone alveolus and implanted roots.

Dental transplants and implants have been carried out for several decades and a variety of techniques have been described.

Implanting techniques in current use include the following:

a) prostheses on osteo-integrated implants, artificial titanium roots which are stabilized by bony ankylosis. The force of mastication is transmitted to the bone with no dampening because of the absence of alveolodental ligament which is an important factor in protecting teeth against shock, overload and the risk of fracture;

b) transplants or other dental grafts which do not have the disadvantages of the preceding approaches but require extraction of a donor tooth which is available and generally non-functional.

Before embarking on the description of the present invention, a reminder of the physiological conditions regarding the connections of the natural tooth is necessary. The tooth is anchored in a cavity termed the alveolus, in the alveolar bone. The root and bone are anchored together by a ligament principally constituted by bundles of collagen fibers with one end anchored in the bone and the other end in the cementum, a mineralised layer resulting from differentiation of undifferentiated mesenchymal cells to cementoblasts which produce the organic and mineral matrices constituting the cementum. Collagen fibers are perpendicularly inserted in this cementum, and are included parallel to the cementum surface, forming a network.

In order to be functional and accepted, ideally, implanting an artificial tooth must anatomically and histologically reproduce the support structures of natural teeth, i.e., the cementum, the alveolodental ligament, and the alveolar bone, with all of their components: differentiated or undifferentiated cells, collagenic fibers and other fibers (elastic, oxytalan, elauin), the basic substance, mineralised tissues, vascularisation and innervation.

The patent application EP-A-734712 (Kanebo Ltd) describes a method for carrying out an implant by applying a layer of cementum particles to the surface. However, such implant does not present collagen fibers perpendicularly inserted in the surface of the neoformed cementum, necessary to the attachment of said implant with the alveolar cavity.

In order to stimulate the reformation of alveolodental ligaments on the curetted dental roots, Hanes et al. ("Cell and Fiber attachment to demineralised cementum from normal root surfaces" Vol. 60, no. 4, pages 188–198), have studied the effect of citric acid on its surface; the cementum or dentin fibers removed by demineralisation can bind by "splices" to the collagen fibers in the surrounding tissues. But there is no "neo-cement" and the fibers stand much less dense than a normal desmodont The fibroblasts, ligament generators, cementoblasts and osteoblasts bordering the alveolar bone result from differentiation of undifferentiated mesenchymal stem cells which are normally sited in the connective tissues surrounding the blood vessels. They can be found on the surface of the roots of extracted teeth and/or in the alveolus of extracted teeth or in the ligaments of a tooth or in other tissues, which may or may not be buccal connective tissue.

The invention results from a demonstration that under certain biological and mechanical stimulation conditions, the natural physiological environment of the root described above can be reconstituted from a culture of undifferentiated mesenchymal stem cells.

The proposed invention can thus enable teeth lost in the majority of clinical situations to be replaced with permanent artificial teeth connected to the jaws by the same tissue elements as natural teeth, i.e., a cementum, an alveolodental ligament and an alveolar bone and enabling normal attachment of the gingivae to the neck of the implant. These four elements are constituents of the periodontal tissue which can thus fulfil its normal physiological role, namely dampening the stresses of mastication, preventing overloads, and adapting the position and mobility of the tooth to the average load it receives.

The present invention provides a method of manufacturing a dental implant comprising:

preparing an implant composed of a root portion and a crown portion and constituted by a biocompatible material in a shape which is adapted to an extracted tooth;

immersing the root portion of said implant in a culture of undifferentiated mesenchymal stem cells in a culture medium the composition of which allows differentiation into cementoblasts and fibroblasts, over a period which is sufficient for said differentiation and for adhesion of cementoblasts to the root portion and the formation of a first layer of cementum and an alveolodental ligament primordium attached to said cementum;

recovering the implant carrying differentiated tissues affixed to its root portion.

The choice of implant is governed by different criteria. The first criterion is its morphology. This depends on the volume of dentin (ivory) in the tooth to be replaced, i.e., the total volume less the enamel and cementum. The desired shape is obtained, for example, by comparison with the extracted tooth; it is then customised to the exact shape of the tooth to be replaced. The desired shape can also be obtained from radiological or tomodensitometric data or the like. The implant is then shaped from a block constituted by a selected material using an N/C machine or any other means. A few basic shapes may also be satisfactory in a majority of cases; they will have a variety of lengths, diameters or tapers, with round or oval cross sections.

The choice of implant material in the method of the invention is guided firstly by the biological and immunological acceptability of said material in the mouth, and secondly by its performance as a support for cementoblast adhesion. The material of the implants must be biocompatible and must be sufficiently strong mechanically to avoid the risk of fracture; the surface must also be roughened to facilitate cell adhesion, and finally its color must be close to that of the natural tooth. Known materials can be envisaged for the material of the implant, such as titanium, alloys or ceramics, for example zirconia. Natural devitalised teeth obtained from any source may also be used. Such materials have been described in Periodontology 2000 (1998) 17: 7–21.

In addition to the root portion which is brought into contact with the undifferentiated mesenchymal culture, the dental implant used in the method of the invention comprises a crown portion which can be capped by a crown of resin, a composite, or a metal or ceramic alloy. Grooves are provided in the crown portion of the implant to stabilise the sutures which hold the implant in its alveolus on placing it in the mouth. With the implant viewed occlusally a groove can, for example, occupy one diameter and two others can cross this diameter at a right angle at a point equidistant from the center and from the circumference. However, these grooves can be disposed differently without disturbing the ergonomics of the system, as will be shown in Example 3 below.

Finally, the implant used in the method of the invention can comprise a stent which is coaxial with the tooth and fixed on its crown portion to facilitate manipulation and subsequent re-implanting in the mouth.

One of the essential characteristics of the method of the invention is the formation, by in vitro cell culture in the presence of the implant the shape and material of which has been selected using the criteria described above, of a layer of cells and tissues adhering to the root portion of the implant. These cells and tissues exist naturally between the root of the tooth and the alveolar bone; thus the physiology of re-implanting in the mouth is very similar to natural conditions.

It is well known that fibroblasts are the dominant cell type in all connective tissues in the human body and in particular are the essential cells of the tissues of the periodontal ligament. The differentiated cells of the periodontal tissue, namely cementoblasts, fibroblasts and osteoblasts, originate from differentiation of undifferentiated cells which are the mesenchymal stem cells. These cells are normally found in the connective tissues surrounding the blood vessels. They can be removed from the surface of the roots of extracted teeth if they have not been contaminated and/or from the alveolus of extracted teeth, or from the ligament of a tooth by removal using a trocar needle, or from explants of buccal connective tissue.

These stem cells exist in other connective tissues of the body, and can thus be removed from other, non-buccal, sites.

The removed undifferentiated cells are cultured under conventional conditions, for example in a petri dish, in Falcon type culture dishes, or in rolling bottles.

The removed undifferentiated mesenchymal cells are cultured in a medium the composition of which enables growth and differentiation into fibroblasts and cementoblasts. Such media are conventional media for culturing fibroblastic animal cells such as those described, for example, in the review article by S. Pitaru et al., in J. Periodont. Res. (1994), 29: 81–94. By way of example, DMEM medium (Dulbecco's Modification of Eagle's MEM) (Dulbecco & Freeman, 1959: Morton, 1970) supplemented with foetal calf serum can be used. This medium is supplemented with antibiotics and antifungal agents. The culturing cells are biologically stimulated by adding to the medium the molecules or compositions required for development and differentiation of the cementoblasts and fibroblasts. They may be growth factors. Examples which can be cited are: PDGF, IGF, proteins from the embryonic enamel organ, bFGF, and other molecules having an anabolising effect on periodontal tissue, for example nifedipine, vitamin C or avocado, maize and/or soya nonsaponifiable matter. This list is not limiting.

The patent application WO 97/45533 (Rutherford) discloses methods for regenerating different tissues and in particular, oral and dental tissues using ex vivo culture of cells. More specifically, it relates to a culture of cementum cells or cells derived from the alveolodental ligament. It also relates to the use of structural matrix to enable tissue differentiation.

When the cell density reaches 105 cells/ml, the cells are transferred to a culturing apparatus for immersion of the root portion of the implant to be treated. The appropriate culturing apparatus also forms part of the invention and is described below.

The implant is then positioned in the culturing apparatus until a layer of cementoblasts adhering to its root portion is obtained which produces a first layer of cementum with connective fibers inserted in this cementum, and a second layer containing fibroblasts and collagen in the course of being formed.

After immersion in the culture medium for 15 to 30 days in the apparatus, the implant is then recovered and "implanted" in the mouth in the alveolus under the conditions described in the protocol of Example x below.

In the method of the invention, biological stimulation of cell differentiation of the undifferentiated mesenchymal cells can be completed by "physiological" mechanical stimulation. This is effected by applying a periodical force to the implant when it is immersed in the culturing cell. This can also be achieved by a periodical stirring applied to the culture apparatus, the implant being then fixed by any appropriate means. One should apply a moderate motion between the implant and the artificial alveolus included in the apparatus containing the culture medium in which the implant is immersed. Stirring can be an alternating motion with a period in the range 1 to 60 seconds without restricting this method to that range, and with an amplitude in the range 0.005 to 2 mm; the displacement can be horizontal, i.e., orthogonal to the axis of the implant, vertical, i.e., longitudinal to the axis of the implant, or a combination of the two. It can also be a rotary motion.

The motion applied to the implant in its culture medium has a double function, conferred by the relative motion between the implant and the artificial alveolus formed by the porous membrane. The first function is to create a functional stimulation of the cells under culture, which increases their proliferation, differentiation, synthesising activities (cementum and collagen) and physiological orientation of the structures being formed. The second function of this agitation is to agitate the cell culture, as it is recommended when culturing any eukaryotic cells; this aerates the cells better and also circulates the medium and nutrients in the cell environment, encouraging their development.

This agitation can be effected using any system which can adjust the period and amplitude within the limits defined above. It may be a mechanical, electrical, hydraulic or pneumatic system, this list not being limiting. Different embodiments can be envisaged in this regard: the motion can be applied to the implant alone, via a stent which is fixed to crown portion of the implant; it can also be applied to the system assembly containing the cell culture in which the root portion of the implant is immersed. Finally, it can be applied to cell culture, the implant proper being fixed to a support by a stent which is integral with the crown portion. What is desired in this mechanical agitation is a relative motion of the root portion of the implant and the culture medium in which it is immersed, with the period and amplitude conditions described above which can satisfy the two functions, cell stimulation and cell agitation.

The present invention also relates to a cell culturing apparatus for preparing a dental implant.

More particularly, when referring to FIG. 1, the present invention provides a cell culturing apparatus for preparing a dental implant (30) constituted by a root portion (31) and a crown portion on which a stent (32) is fixed to enable it to be manipulated and subsequently placed in the mouth, said apparatus comprising:

a culture dish (10) the shape of which comprises a longitudinal axis;

said culture dish being closed by a cover (11) and comprising a porous wall (20) delimiting a first space (21) containing the cell culture medium, and a second space (22) containing the cells being cultured, and in which the root portion of the implant is immersed, said wall having a configuration such that a gap of 0.1 to 5 mm, ideally 1 mm, is left between the root portion of the implant and the wall, creating an artificial alveolus.

Said apparatus comprises a means for agitating the implant in said artificial alveolus using an alternating motion with a period in the range 5 to 60 seconds and with an amplitude in the range 0.005 to 2 mm, or in a rotary motion with a period in the range 1 to 60 seconds. This agitation means can be mechanical, hydraulic or magnetic to confer an alternating or rotary motion on the stent. Alternatively, the apparatus may comprise a means for agitating of the culture dish and a means for maintaining the dental implant.

The present invention also relates to a dental implant which can be obtained by a method as described above and which can reconstitute, on the root surface of the implant, the different constituent tissues of the periodontal tissue, namely the cementum and the ligaments connecting the cementum to the alveolar bone. This implant or artificial tooth is constituted by an inert biocompatible material the shape of which is adapted to that of the extracted tooth. The dental implant of the invention will thus comprise a crown portion and a root portion which, before implanting in the mouth, will be coated with differentiated cells which can then allow more complete formation of the cementum and ligament in situ. A dental implant of the invention can ensure complete reconstitution of a normal periodontal tissue system supporting the implant in two to three months.

Finally, the invention provides a method for replacing lost or compromised teeth by artificial implants on which biological tissues are affixed using a suitable cell culture technique, to then obtain mouth cicatrisation by cementum and ligament between the bone aveolus and implanted roots.

The examples and figures below are not limiting and serve to illustrate the invention and to enable the skilled person to carry it out directly or to carry out any functional equivalent to produce the dental implant the surface of the root portion of which is lined with cementoblasts forming a cementum and collagen fibers, and fibroblasts producing collagen fibers reconstituting an alveolodental ligament primordium.

(1) shows the occlusal view;

(2) is a perspective view.

Figure 2A:
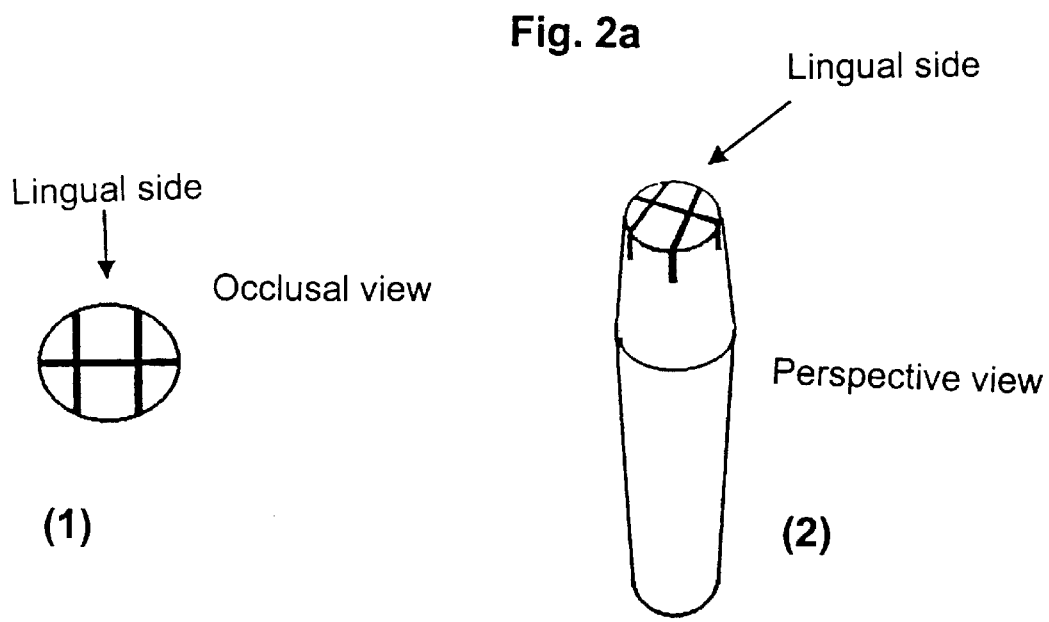
FIG. 2a shows the disposition of occlusal grooves for stabilising sutures which retain the implant.
Figure 2B:
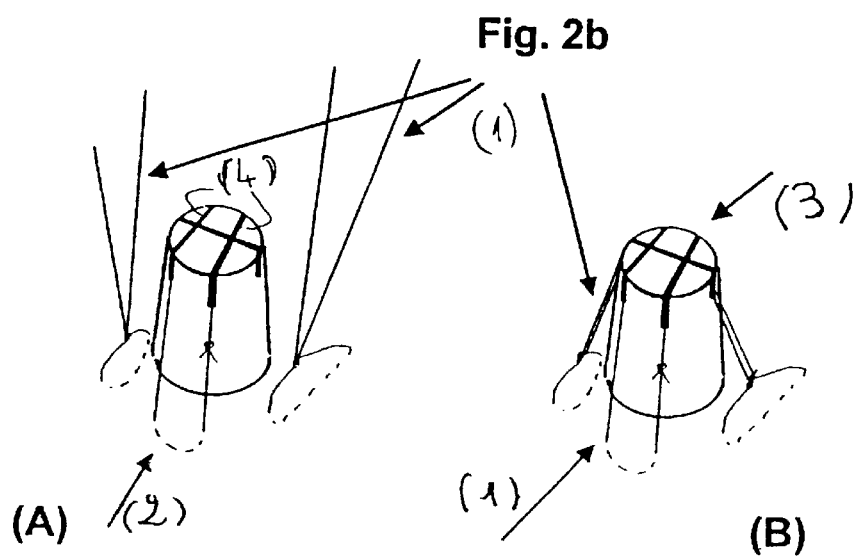

FIG. 2b shows diagrams showing the crown portion of the implant emerging from the gum; (A): the proximal sutures have not yet been connected through the mesio-distal groove; (B): the knots have been tied.

EXAMPLE 1

Cell Culture Protocol Aimed at Creating a Periodontal Tissue in Vitro

1) Removal of Cells

The target cell population is that of undifferentiated mesenchymal stem cells which are normally located in the connective tissues and in the endosteal spaces surrounding the blood vessels.

Removal can be carried out:

by scraping uncontaminated surfaces of extracted tooth roots using a sterile scalpel;

by cleaning out the alveolus of extracted teeth, also uncontaminated;

by biopsy of periosteal or supra-periosteal tissues;

by removing other buccal or non-buccal connective tissues.

2) Transport of Samples

The tissues are placed in tubes containing a Dulbecco's modification of Eagle's MEM (DMEM) type culture medium with:

20% foetal calf serum (FCS);

streptomycin(100000 mg/ml);

fungizone (1%);

buffer system;

for a maximum period of 24 hours at 4° C.

3) Primary Culture the biopsies are reduced to fragments of about 1×1×1 mm using a scalpel;

the explants obtained are placed in 60 mm culture dishes containing:

DMEM;

20% FCS;

1% penicillin-streptomycin;

1% fungizone incubated at 37° C. in moist air containing 5% CO2;

after 3 days, the medium is replaced by DMEM+10% FCS, with no antibiotics.

4) Subcultures

When cellular proliferation around the explants is evident, and the cells arrive at confluence, they are detached with 0.05% trypsin in a phosphate buffered serum for 10 min, then spread into further culture dishes;

the medium is the same;

after 3 or 4 passes, the quantity of fibroblasts obtained is sufficient to seed the root.

5) Adhesion Phase

In the same medium with added growth factors, the cells are placed around the artificial root in an artificial alveolus leaving only ½ to 1 mm of space.

The root and its contents are connected by a suitable plug.

The assembly is placed horizontally to encourage adhesion to the surface of the root, turning by 120° every 15 minutes.

6) Stimulated Culture Phase in the Apparatus

After three hours, the root is placed vertically in the culturing system with physiological stimulation, renewing the medium to which growth factors have been added.

7) Transport Condition

After 15 days, the apparatus is used to transport the implant for implanting. Depending on the transport time, the system is kept at 37° C. or reduced to 4° C.

The implant coated with cementum and ligament is removed from the culturing apparatus and immediately placed in the prepared alveolus, then sutured.

EXAMPLE 2

Production of a Cell Culturing Apparatus

Figure 1:
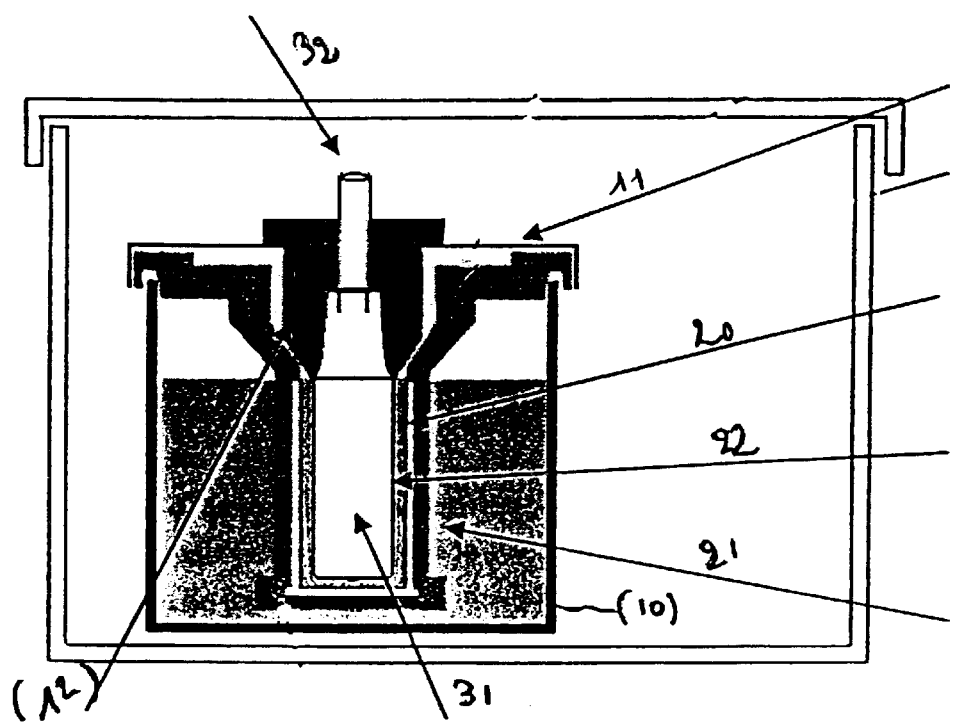
FIG. 1 shows a diagram of an organotypical culturing apparatus surrounding artificial roots, with biological and physiological (mechanical) stimulation to obtain cementogenesis and ligamentogenesis and is described in detail in Example 2.

FIG. 1 represents the principal of such an apparatus and the numbers in brackets refer to the different elements of this figure.

The dental implant (30) is constituted by a root portion (31) and a crown portion on which a fixing stent (32) allows it to be agitated and allows its subsequent manipulation and its positioning in the mouth. The apparatus comprises:

a culture dish (10) the shape of which includes a longitudinal axis;

said culture dish is closed by a slightly flexible cover (11) and contains a porous wall (20) delimiting a first space (21) distal with respect to the root portion (31) and containing the cell culture medium, and a second space (22) containing cells being cultured, and in which the root portion of the implant is immersed. The configuration of the wall delimiting the two spaces is such that the second space (22) is of a shape and dimension such that a gap of 0.1 to 5 mm (ideally 1 mm) is left between the wall (20) and the root portion of the implant (31) to create an artificial alveolus.

The culture dish (10) can have a circular cross section or it can be of any other shape. Its cross section must be sufficient to accept the implant root, the second space (22) containing the cells under culture and the first space (21) containing the remainder of the culture medium. Dish (10) is more than 10 mm higher than the total height of the implant, i.e., about 50 mm high. In its apical portion, a space must be reserved for circulation of the culture medium and the stent must be accessible to the outside of the dish so cover (11) is provided with a removable fixing ring.

Cover (11) of the dish must nest on the dish under conditions which maintain the sterility of the culture medium; this is effected, for example, using a cover similar to that of a Petri dish. Any other means for fixing cover (11) to dish (10) can, of course, be envisaged by the skilled person provided that the functional characteristics of this apparatus are retained, namely immersion of the root portion in a cell culture, said culture forming an artificial alveolus with a cross section in the range 0.1 to 5 mm beyond the root portion (31) of the implant.

The cover can comprise a central portion (12) in which the fixing stent (32) of the implant can be inserted via a fixing ring which when placing the implant in the mouth, enables withdrawal from the culturing dish, which can also be used for transport in a special heat regulated container, protecting it from any contamination and stabilised in a vertical position.

The apparatus of the invention also comprises a means for agitating the implant in an alternating motion with a period in the range 5 to 60 seconds and with an amplitude in the range 0.1 to 2 mm or in an alternating rotary motion with a period in the range 5 to 60 seconds.

This agitation has a double function: the usual function of agitating a cell culture to provide correct aeration and a good distribution of the culture medium and its nutrients over the cells in suspension or adhering cells; the second function is to create mechanical stimulation which leads to the desired cell differentiation into cementoblasts and fibroblasts, generating ligaments.

This agitation can be provided in a number of manners:

the motion can be applied to the implant using a mechanical, hydraulic or magnetic agitator applied to the stent (32). In this case, the cover (11) of dish (10) must be provided at its central portion with a stent fixing means (32) to provide an autonomous motion to the implant in the dish/cover assembly. To this end, a means for fixing the stent in the central position of the cover is provided, or the cover itself (11) must be sufficiently flexible to carry out this motion the motion can be provided to the dish/cover assembly, the implant itself being fixed on a support by any suitable means; here again, cover (11) or the means for fixing the stent to the dish must have sufficient flexibility to enable the motion to be carried out.

The culture dish (10) contains two spaces:

a first space (21) contains the culture medium. This can, for example, be a DMEM type medium with added foetal calf serum and to which the different growth factors or molecules required for growth and cellular differentiation are added;

a second space (22) contains the cell culture seeded with the pre-culture of mesenchymal cells as described above.

These two spaces are separated by a porous membrane or wall or a pierced wall stabilising a microporous membrane, with a rigidity which is sufficient to endow it with the desired stable shape.

This wall has the following pore size and shape characteristics:

a) the pore size is such that the culture medium containing its nutrients and its growth factors diffuse into the second compartment (22) while the cells remain confined in said compartment.

The pore size will thus be in the range 0.2 to 2 microns. Any type of material which can provide this pore size and the relative rigidity required for characteristic b) below can be used.

Examples are polycarbonate, cellulose acetate (millipore filter, millicell), etc.

b) the membrane or its mounting system is fixed to dish (10) at a level which is higher than the level of the culture medium. It can be joined to the edges of the dish (10) in the shape of a cone, for example. Further, it creates in the dish (10) an artificial alveolus of similar shape to the root portion of implant (31) so as to create a space 0.1 to 5 mm, preferably 1 mm wide between the implant root and said porous wall.

The membrane with its mounting system must be detachable from the bottom of the dish while remaining integral with the cover which is itself connected to the implant. Thus when the cover is raised, the first space (21) is completely accessible to modify or change the medium.

The apparatus assembly, comprising the dish (10), the cover (11), the wall (20) and the implant (30), is placed in an incubator at 37° C. containing 95% of moist air and 5% of $CO_2$.

EXAMPLE 3

Implant Structure Example

The implant of the desired shape is formed from a biocompatible material as described in Periodontology 2000 (1998), 17: 7–21.

With a view to subsequent implanting, grooves are formed in the crown portion of the implant to stabilise suture threads which retain the implant in its alveolus on placing it in the mouth. Alternatively, these grooves or fixing rings can be directly disposed on a temporary crown made in resin and fixed to the crown portion of the implant. The invention also relates to an implant stabilized in mouth by temporary crowns especially prepared for retaining the suture threads by said grooves or fixing rings. These grooves can measure 1 mm wide and 2 mm deep. FIG. 2a shows an example of their disposition. This disposition enables suture threads (1) to be passed as shown in FIG. 2a. One thread is mattress sutured into the vestibular gum (2) and into the lingual gum (3) and pass twice via the occlusal face of the implant in the two vestibulolingual grooves (4). This can retain the implant and can also adjust the height of the free edge of the gum with respect to the implant. A simple suture is placed to bring the gingival papillae distal to the implant together, 5 cm of each thread being left free after the knot. The same operation is carried out mesial to the implant, leaving threads 20 cm long. Then each mesial thread is knotted with each distal thread by passing via the same mesiodistal groove of the implant. The implant is thus secured by three sutures. A circular cervical suture is often necessary to bring the gingival edge closer to the periphery of the implant, and to prevent embedding of the implant when it is positioned at the level of a maxillary sinus.

EXAMPLE 4

Implanting in the Mouth

The dental implant of the invention is placed in the mouth after about 15 days of culture in the apparatus described above.

A protocol for placing a dental implant of the invention in the mouth comprises a number of phases and can be as follows:

a) buccal cleansing and use of antiseptic and antiseptic mouthwashes: the buccal bacterial charge must be reduced to a minimum to avoid contamination of the cicatrisation zone.

b) Preparation of alveolus: the ideal situation is to have extracted the tooth to be replaced about two weeks in advance. The alveolus then only needs to be carefully curetted. The partial gingival cicatrisation can act to properly "set" the neck of the implant once in place, to obtain a satisfactory seal of the wound at this point and cicatrisation via the epithelium with a short join. Epithelial cells do not migrate along the root. In other cases where the alveolus does not already exist, it must be prepared, preferably two weeks in advance after removal of a mucoperiosteal flap. The alveolus is prepared using drills with increasing diameters, slowly and with irrigation with sterile isotonic serum. The drills are adapted to the standard implant type shapes. Some drills work only along their axis, others enable the alveolus to be "shaped" suitably with an edge on the lateral faces. They result in an alveolus which is always larger than the implant, leaving a space of at least one millimeter, so that the bone is not in direct contact with the implant. At the sinuses, after lifting a mucoperiosteal flap and perforation of the bone wall, the sinus mucosa is removed with special detaching devices. This preparation has to be carried out about two weeks before implanting, to enable the sinus mucus to grow back with no risk of perforating it.

c) Models of neutral and sterile (sterilisable) material are made in the exact shape of the implants, including the complete crown, either standard or customised to provide an ideally positioned implant, enabling the preparation of the alveolus to be checked. They comprise a holding tab in the middle of the vestibular face of their crown portion. A second type of model comprises the complete volume of the crown and a root of the length to be prepared but with a reduced diameter. It is used after the first drilling to check the positioning and possibly to modify it on enlarging the alveolus. The implant root may not be entirely contained in the available bone volume. If it goes beyond the bone surface vertically or horizontally, this does not prevent cicatrisation and can even generate a spontaneous increase in the bone volume around the non embedded root provided that the surfaces which are not embedded in the bone remain sub-mucous. The same phenomenon occurs in the sinus.

d) The implant, removed from its culture dish, held by its stent and fixing ring, is immediately positioned in the alveolus, preferably without contact with anything, in particular an instrument, a compress, a buccal mucous, the tongue, saliva . . . . It is maintained in place by sutures in the gum either side of the implant and sliding in the groove prepared in the emerging "crown" portion. Sutures must also ensure that the gum seals to the neck of the implant. The sutures are left in place for about 15 days. No other support, in particular those which are rigid with the other teeth, is used. The crown portion of the implant, reduced at this stage as it has not been provided with its temporary crown, must not come into contact with the antagonistic teeth.

e) Temporary crown: standard temporary crowns can be sealed to the implants after two weeks. They are adjusted to have an occlusal contact solely in a centered intermaxillar relationship or with maximal intercuspation. Their shape and appearance can be adjusted by adding or subtracting resin by molding. Check-ups are indicated for two months to monitor the progress of the implant and to avoid any overloading.

f) The proper prostheses can be attached to the implants about 3 months after positioning. Conventional techniques can be used. These implants behave exactly like natural teeth. The ligament which connects them to the bone dampens stresses, prevents overloading, reduces impact, and limits the risk of fracture of the prosthetic crowns and the implants themselves.

What is claimed is:

1. A method of manufacturing a dental implant comprising:

preparing an implant composed of a root portion and a crown portion and constituted by an inert biocompatible material in a shape which is adapted to an extracted tooth;

immersing the root portion of said implant in a culture of undifferentiated mesenchymal cells with an apparatus comprising a culture dish (10) the shape of which comprises a longitudinal axis, said culture dish being closed by a cover (11) and containing a porous wall (20) delimiting a first space (21) containing the cell culture medium, and a second space (22) containing the cells being cultured, and in which the root portion of the implant is immersed, said wall having a configuration such that a gap 0.1 to 5 mm is left between the root portion of the implant and the wall, creating an artificial alveolus, the culture of mesenchymal undifferentiated cells as above-mentioned and in a culture medium the composition of which allows differentiation into cementoblasts and fibroblasts, over a period which is sufficient for said differentiation and for adhesion of cementoblasts to the root portion and the formation of a first layer of cementum and of an alveolodental ligament primordium attached to said cementum;

recovering the implant carrying differentiated tissues affixed to its root portion.

2. A method according to claim 1, characterized in that the mesenchymal stem cells are removed from connective tissues and pre-cultured in a petri dish to a cell density of $10^5$ cells per ml then brought into contact with the root portion of the implant in a culture medium and in a culturing apparatus as the one defined in claim 1.

3. A method according to claim 2, in which differentiation of cells to cementoblast and fibroblast is stimulated by adding specific growth factors to the culture medium, or any molecules stimulating cellular differentiation of the mesenchymal cells.

4. A method according to claim 1, in which the culture undergoes physiological stimulation by agitating the implant in the culturing apparatus, said agitation having the effect of stimulating the development of cells and tissues on the inert material.

5. A method according to claim 4, characterized n that the agitation is an alternating motion with a period in the range 1 to 60 seconds and an amplitude in the range 0.005 to 2 mm, or a rotary motion with a period in the range 1 to 60 seconds.

6. A cell culturing apparatus for preparing a dental implant (30) constituted by a root portion (31) and a crown portion on which a stent (32) is fixed to enable it to be manipulated and subsequently placed in the mouth, said apparatus comprising:

a culture dish (10) the shape of which comprises a longitudinal axis;

said culture dish being closed by a cover (11) and containing a porous wall (20) delimiting a first space (21) containing the cell culture medium, and a second space (22) containing the cells being cultured, and in which the root portion of the implant is immersed, said wall having a configuration such that a gap 0.1 to 5 mm is left between the root portion of the implant and the wall, creating an artificial alveolus.

7. An apparatus according to claim 6, in which the central position of the cover (11) comprises means for fixing the stent (32) which latter is integral with the implant.

8. An apparatus according to claim 6, further comprising means for agitating the implant in said artificial alveolus using an alternating motion with a period in the rang 5 to 60 seconds and with an amplitude in the range 0.006 to 2 mm or in a rotary motion with a period in the range 1 to 60 seconds.

9. An apparatus according to claim 7, further comprising means for agitating the implant in said artificial alveolus using an alternating motion with a period in the rang 5 to 60 seconds and with an amplitude in the range 0.006 to 2 mm or in a rotary motion with a period in the range 1 to 60 seconds.

10. An apparatus according to claim 8, in which the agitation means is mechanical, hydraulic or magnetic and endows the stent (32) with an alternating or rotary motion.

11. An apparatus according to claim 8, in which the cover (11) is slightly flexible to permit the alternating motion.

12. An apparatus according to claim 8, in which the agitating means is provided by an alternating or rotary motion of the dish (10).

13. An apparatus according to claim 6, in which the pore size of the porous wall (20) is in range 0.2 to 2 microns.

14. An apparatus according to claim 13, in which the wall (20) is fixed to the dish (10) above the level of the cell culture medium.

15. A dental implant which can be obtained by a method according to claim 1, constituted by an inert biocompatible material in a shape which is adapted to an extracted tooth, wherein the surface of the root portion (31) is lined with cementoblasts forming a cementum and with collagen fibres, and fibroblasts producing collagen fibres reconstituting an alveolodental ligament primordium.

16. An implant according to claim 15, in which grooves are disposed on the crown portion to stabilise sutures which retain the implant in its alveolus when placing the implant in the mouth.

17. An implant according to claim 16, wherein grooves can be directly disposed on a temporary crown fixed to the crown portion of the implant.

18. A dental implant produced by a method according to claim 1.

19. A dental implant produced by an apparatus of claim 6.

* * * * *